United States Patent [19]

Fujii et al.

[11] Patent Number: 4,898,876
[45] Date of Patent: Feb. 6, 1990

[54] BENZOYLPIPERAZINE ESTERS AND A PROCESS FOR THEIR PRODUCTION

[75] Inventors: Setsuro Fujii, Toyonaka; Eizou Hattori, Sakado; Mitsuteru Hirata, Tokorozawa; Koichiro Watanabe, Higashi-Murayama; Kazuhiro Onogi, Iruma; Masahiko Nagakura, Sayama, all of Japan

[73] Assignee: Kowa Co., Ltd., Nagoya, Japan

[21] Appl. No.: 796,525

[22] Filed: Nov. 12, 1985

[30] Foreign Application Priority Data

Jun. 25, 1982 [JP] Japan ................................ 57-109192
Apr. 28, 1983 [JP] Japan ................................ 58-75868

[51] Int. Cl.$^4$ ................................ C07D 241/04
[52] U.S. Cl. ................................ 544/391; 544/235; 544/237; 544/283; 544/353; 544/363; 544/365; 544/373; 544/375; 544/377; 544/380; 544/387
[58] Field of Search ............... 544/235, 237, 283, 353, 544/365, 367, 373, 375-377, 380, 387, 391, 363

[56] References Cited

U.S. PATENT DOCUMENTS

T620,005 10/1986 Fujii et al. ............... 544/391
4,443,603 4/1984 Fujii et al. ............... 544/373

FOREIGN PATENT DOCUMENTS

71433 2/1983 European Pat. Off. .
158737 7/1981 Japan .
58-21622 2/1983 Japan .

OTHER PUBLICATIONS

Mach, *Advanced Organic Chemistry*, 2nd ed., McGraw-Hill N.Y. (1977) pp. 364-365.
Journal of Biochemistry, vol. 62, No. 4, 1967, pp. 408-418.
English Abstract of Japanese 158737.
Kohjin Co. Ltd., Chem. Abstracts 99:38809 (1983).
Kowa Co. Ltd., Chem. Abstracts 96:180955 (1982).

*Primary Examiner*—Donald G. Daus
*Attorney, Agent, or Firm*—Oblon, Spivak, McClelland, Maier & Neustadt

[57] ABSTRACT

A benzopylpiperazine ester of the following formula:

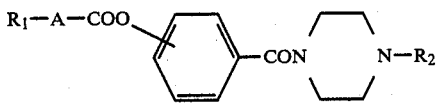

wherein A represents a single bond or an alkylene group, vinylene group, —O—alkylene group or methine group, $R_1$ represents a bicyclic carbon ring residue which may be substituted with a lower alkyl group, lower alkoxy group, oxo group or nitro group or a halogen atom, or may be partially saturated; a fluorene residue which may contain an oxo group; a fluorenylidene group; an anthracene residue; a phenanthrene residue which may be substituted with a lower alkyl group, or may be partially saturated; a benzofuran residue or thianaphthene residue which may be substituted with a lower alkyl group or lower alkoxy group; a benzopyran residue or benzoazine residue which may be substituted with an oxo group or phenyl group and partially saturated; a phthalimide residue; a benzodiazine residue; an isozazole residue which may be substituted with a lower alkyl group or phenyl group; or an alkylene dioxybenzene residue or xanthene residue; and $R_2$ represents an alkyl group, cycloalkyl group, cycloalkylalkyl group or aralkyl group, excepting the case where A is a single bond, $R_1$ is

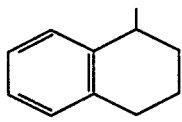

and $R_2$ is a methyl group, exhibits excellent chymotrypsin inhibitive activity.

14 Claims, No Drawings

BENZOYLPIPERAZINE ESTERS AND A PROCESS FOR THEIR PRODUCTION

BACKGROUND OF THE INVENTION

1. Field of the Invention

This invention relates generally to novel benzoylpiperazine esters and to a process for producing such esters.

More particularly, the invention is concerned with a benzoylpiperazine ester represented by the following formula (I):

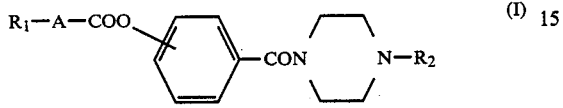

wherein A represents a single bond or an alkylene group, vinylene group, —O—alkylene group or methine group; $R_1$ represents a bicyclic carbon ring residue which may be substituted with a lower alkyl group, lower alkoxy group, oxo group or nitro group or a halogen atom, or may be partially saturated; a fluorene residue which may contain an oxo group; a fluorenylidene group; an anthracene residue; a phenanthrene residue which may be substituted with a lower alkyl group, or may be partially saturated; a benzofuran residue or thianaphthene residue which may be substituted with a lower alkyl group or lower alkoxy group; a benzopyran residue or benzoazine residue which may be substituted with an oxo group or phenyl group and partially saturated; a phthalimide residue; a benzodiazine residue; an isooxazole residue which may be substituted with a lower alkyl group or phenyl group; or an alkylene dioxybenzene residue or xanthene residue; and $R_2$ represents an alkyl group, cycloalkyl group, cycloalkylalkyl group or aralkyl group, excepting the case where A is a single bond, $R_1$ is

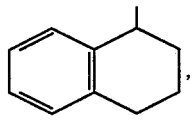

and $R_2$ is a methyl group.

DESCRIPTION OF THE PRIOR ART

The present inventors have previously discovered that various phenyl esters have excellent chymotrypsin inhibitive effects (see Japanese laid-open patent specification No. 158737/1981).

The inventors have further synthesized analogous compounds to study their pharmacological effects. In the studies leading to the present invention, it has been found that novel benzoylpiperazine derivatives represented by the formula (I) above and acid addition salts thereof exert more excellent chymotrypsin inhibitive effects.

SUMMARY OF THE INVENTION

Accordingly, it is one object of the invention to provide benzoylpiperazine esters of the formula (I) which possess substantially superior chymotrypsin inhibitive activity and can be widely used, for example, as medicines such as those for the therapy of pancreatopathy.

Another object of the invention is to provide a process for producing such esters.

DETAILED DESCRIPTION OF THE PREFERRED EMBODIMENTS

The compounds of the formula (I) of the invention can be produced by esterification of carboxylic acids of the formula (II) and substituted phenols of the formula (III), for example, in accordance with the following reaction scheme.

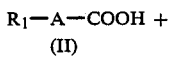

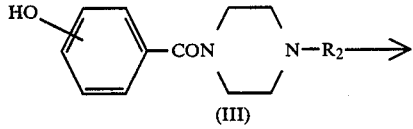

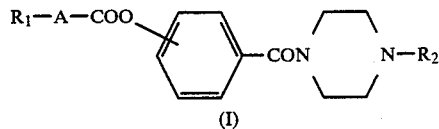

wherein the symbols each have the same meaning as above.

The esterifying reaction between the compounds of the formulae (II) and (III) is carried out using any conventional techniques. Suitable techniques useful in the invention include a method of reacting a reactive derivative of the compound (II), for example, an acid halide, an acid anhydride, a mixed acid anhydride, an active ester, an active azide or the like, with the compound (III), and a method of reacting the compounds (II) and (III) in the presence of a dehydrating agent such as dicyclohexyl carbodiimide.

Eligible bicyclic carbon ring residues for the symbol $R_1$ in the formula (I) include such residues as derived from an indene group, naphthyl group and benzosberyl group. Eligible benzoazine residues include such residues as derived from quinoline and isoquinoline. Eligible benzodiazine residues include such residues as derived from quinoline and quinoxaline. Eligible alkylene dioxybenzene residues include such residues as derived from methylene dioxybenzene and benzodioxane.

The compound (I) obtained in this way may be further converted by a conventional method to an inorganic acid salt, for example, of hydrochloric acid, sulfuric acid, phosphoric acid or hydrobromic acid; and an organic acid salt, for example, of acetic acid, propionic acid, maleic acid, fumaric acid, tartaric acid, citric acid, methane sulfonic acid, benzene sulfonic acid or toluene sulfonic acid.

The chymotrypsin inhibitive activity of the compounds according to the invention will be readily understood by reference to the following test results.

MEASURING METHOD

A solution prepared by mixing 0.1 ml of a dimethylsulfoxide solution containing a compound to be tested, 0.1 ml of water and 0.1 ml of a buffer solution containing 10 ug/ml of chymotrypsin (0.1M tris-hydrochloric acid buffer solution, pH 8.0) was incubated for 10 minutes by the method of Muramatsu et al. [see The Journal of Biochemistry, 62, 408 (1967)]. 0.2 ml of a buffer solution containing 25 mM of an acetyl-L-tyrosine ethyl ester was mixed with the above-prepared solution and reacted at 30° C. for 30 minutes. The amount of the remaining substrate was determined by causing the same to develop color by the Hestrin Method and measuring the absorbance at 530 nm. For comparative purposes, use was made of tosylphenylalanine chloromethyl ketone which was known as a chymotrypsin inhibitor (Comparative Compound I).

RESULTS

The results are as shown in Table 1.

TABLE 1

| Test compounds | | Chymotrypsin inhibitive activity [50% inhibition concentration (M)] |
|---|---|---|
| Present compounds | 1 | $3 \times 10^{-6}$ |
| | 2 | $1 \times 10^{-7}$ |
| | 3 | $9 \times 10^{-7}$ |
| | 4 | $5 \times 10^{-6}$ |
| | 9 | $1 \times 10^{-6}$ |
| | 15 | $8 \times 10^{-7}$ |
| | 17 | $8 \times 10^{-7}$ |
| | 18 | $6 \times 10^{-7}$ |
| | 20 | $5 \times 10^{-6}$ |
| | 21 | $9 \times 10^{-6}$ |
| | 22 | $3 \times 10^{-6}$ |
| | 24 | $5 \times 10^{-7}$ |
| | 30 | $9 \times 10^{-6}$ |
| | 32 | $7 \times 10^{-6}$ |
| | 40 | $1 \times 10^{-6}$ |
| | 65 | $8 \times 10^{-7}$ |
| | 66 | $9 \times 10^{-7}$ |
| | 67 | $8 \times 10^{-7}$ |
| | 68 | $9 \times 10^{-7}$ |
| Comparative compound | I | $5 \times 10^{-4}$ |

Note: The number for each test compound of the invention indicates the corresponding example as will appear hereinafter.

The above disclosure generally describes the present invention. A more complete understanding will be obtained by the following specific examples which are provided for purposes of illustration only and are not construed as limiting to the invention.

EXAMPLE 1

1-Isopropyl-4-[4-(5,6,7,8-tetrahydronaphthalene-1-acetyloxy)benzoyl]piperazine.hydrochloride To a 20 ml ethyl acetate solution containing 1.9 g (10 mmol) of 5,6,7,8-tetrahydronaphthalene-1-acetic acid, 2.48 g (10 mmol) of 1-(4-hydroxybenzoyl)-4-isopropylpiperazine and 122 mg (1 mmol) of 4-dimethylaminopyridine was added 2.48 g (12 mmol) of dicyclohexyl carbodiimide, and the mixture was stirred at room temperature for 3 hours. Any insoluble matter was then removed by filtration, and the filtrate was extracted up to 20 ml of 1N hydrochloric acid. After being washed with ethyl acetate, the extract was neutralized with sodium hydrogen carbonate and then extracted with ethyl acetate. After being washed with saturated saline water, the extract was dried over sodium sulfate and then concentrated under reduced pressure. Purification of the concentrate on silica gel column chromatography (80 g of silica gel, eluting solution: chloroform-methanol 30:1) gave a colorless oily substance in a quantitative yield, and the oily substance was then dissolved in 20 ml of ethanol. The resulting solution was added under ice cooling, with an ethanol solution containing an equimolar amount of hydrogen chloride, and thereafter, further with ether, thereby obtaining colorless crystals.

| Yield | 2.96 g (64.7%) | | |
|---|---|---|---|
| Melting point | 214–216° C. | | |
| Elementary analysis | as $C_{26}H_{32}N_2O_3 \cdot HCl$ | | |
| | C | H | N |
| Calculated (%) | 68.33 | 7.28 | 6.13 |
| Measured (%) | 68.30 | 7.24 | 6.28 |

EXAMPLE 2

1-Isopropyl-4-[4-(9-fluorenylidene acetyloxy)benzoyl]piperazine

To a 20 ml chloroform solution containing 2.67 g (12 mmol) of 9-fluorenylidene acetic acid, 2.48 g (10 mmol) of 1-(4-hydroxybenzoyl)-4-isopropylpiperazine and 122 mg (1 mmol) of 4-dimethylaminopyridine was added 2.48 g (12 mmol) of dicyclohexyl carbodiimide, and the mixture was stirred at room temperature for 3 hours. Any insoluble matter which had formed was removed by filtration, and the filtrate was concentrated under reduced pressure. Thereafter, any insoluble matter was removed by filtration using 20 ml of ethyl acetate, and the filtrate was extracted up to 60 ml of 1N hydrochloric acid. After being washed with ethyl acetate, the extract was neutralized with sodium hydrogen carbonate and extracted up to 60 ml of chloroform. After being washed twice with water, the extract was dried over magnesium sulfate and concentrated under reduced pressure to obtain yellow crystals. Recrystallization of the crystals from ethyl acetate-petroleum ether gave yellow prismatic crystals.

| Yield | 56.7% | | |
|---|---|---|---|
| Melting point | 169–170° C. | | |
| Elementary analysis | as $C_{29}H_{28}N_2O_3$ | | |
| | C | H | N |
| Calculated (%) | 76.97 | 6.24 | 6.19 |
| Measured (%) | 76.97 | 6.19 | 5.97 |

EXAMPLE 3

1-Isopropyl-4-[(4-(thianaphthene-2-acetyloxy)benzoyl]-piperazine.methanesulfonate To a 40 ml of chloroform solution containing 2.2 g of 1-isopropyl-4-(4-hydroxybenzoyl)piperazine and 2.0 g of thianaphthene-2-acetic acid was added 2.2 g of dicyclohexyl carbodiimide, and the mixture was stirred overnight at room temperature. Any insoluble matter was then removed by filtration, and the filtrate was extracted with 24 ml of 0.5N hydrochloric acid. After the extract was washed with ethyl acetate, the aqueous phase was neutralized with 2N sodium hydroxide and then extracted with ethyl acetate. The extract was washed with water and dried, followed by removal of the solvent by distillation, to give a crude oily product. The product was further converted in a conventional manner to methanesulfonate, thereby obtaining colorless prismatic crystals.

| Yield | 2.1 g (45.7%) | | |
|---|---|---|---|
| Melting point | 175–177° C. | | |
| Elementary analysis | as $C_{24}H_{26}N_2O_3S \cdot CH_3SO_3H$ | | |
| | C | H | N |
| Calculated (%) | 57.89 | 5.85 | 5.40 |

| -continued |  |  |  |
|---|---|---|---|
| Measured (%) | 57.63 | 5.93 | 5.12 |

EXAMPLES 4–64

The same procedures as in Examples 1–3 were repeated to obtain various compounds shown in Table 2.

TABLE 2

(Ia)

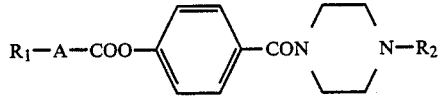

| Example | In Formula (Ia) R$_1$ | A | R$_2$ | Acid Addition Salt | Yield (%) | Appearance | Melting Point (°C.) |
|---|---|---|---|---|---|---|---|
| 4 | [indane] | — | —CH(CH$_3$)$_2$ | HCl | 54.7 | Needle-like pale yellow crystals | 222~226 (decomp.) |
| 5 | CH$_3$O-[indane] | —CH$_2$— | —CH(CH$_3$)$_2$ | HCl | 41.5 | Needle-like colorless crystals | 243~244 |
| 6 | [indane] | — | —CH(CH$_3$)$_2$ | HCl | 61.8 | Platy colorless crystals | 236~237 (decomp.) |
| 7 | [indane-CH$_3$] | — | —CH(CH$_3$)$_2$ | HCl | 80.4 | Colorless crystals | 252~257 (decomp.) |
| 8 | [indene] | —CH$_2$— | —CH(CH$_3$)$_2$ | CH$_3$SO$_3$H | 32.4 | Colorless crystals | 211~212 |
| 9 | CH$_3$O-[indene] | —CH$_2$— | —CH(CH$_3$)$_2$ | HCl | 40.1 | Needle-like pale yellow crystals | 208~210 |
| 10 | CH$_3$O-[indanone] | —CH$_2$— | —CH(CH$_3$)$_2$ | — | 18.2 | Colorless crystals | 131~135 |
| 11 | [tetralin] | —OCH$_2$— | —CH(CH$_3$)$_2$ | CH$_3$SO$_3$H | 29.6 | Colorless crystals | 175~177 |
| 12 | [tetralin] | — | —CH(CH$_3$)$_2$ | CH$_3$SO$_3$H | 58.5 | Platy colorless crystals | 165~167 |
| 13 | [tetralin] | —CH$_2$— | —CH(CH$_3$)$_2$ | HCl | 49.3 | Needle-like colorless crystals | 218~219 |

TABLE 2-continued $$R_1-A-COO-\underset{}{\underset{}{\bigcirc}}-CON\underset{}{\underset{}{\bigcirc}}N-R_2 \quad (Ia)$$

| Example | R₁ (In Formula (Ia)) | A | R₂ | Acid Addition Salt | Yield (%) | Appearance | Melting Point (°C.) |
|---|---|---|---|---|---|---|---|
| 14 | 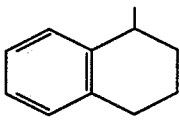 | —CH₂CH₂— | —CH(CH₃)₂ | HCl | 64.6 | Needle-like colorless crystals | 206~208 |
| 15 | 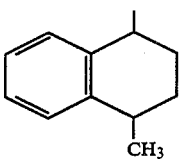 | — | —CH(CH₃)₂ | CH₃SO₃H | 73.7 | Colorless prismatic crystals | 178~180 |
| 16 | 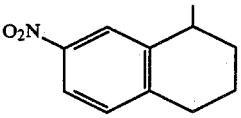 | — | —CH(CH₃)₂ | (COOH)₂ | 8.9 | Yellow prismatic crystals | 135~138 |
| 17 | 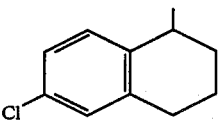 | — | —CH(CH₃)₂ | CH₃SO₃H | 42.7 | Needle-like colorless crystals | 190~196 |
| 18 | 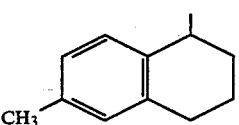 | — | —CH(CH₃)₂ | CH₃SO₃H | 61.9 | Needle-like colorless crystals | 218~219 |
| 19 | 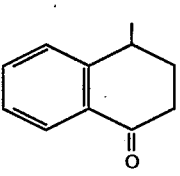 | — | —CH(CH₃)₂ | CH₃SO₃H | 33.0 | Platy colorless crystals | 167~169 |
| 20 | 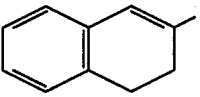 | — | —CH(CH₃)₂ | — | 29.7 | Colorless crystals | 85~87 |
| 21 | 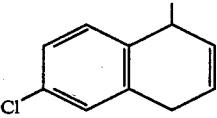 | — | —CH(CH₃)₂ | CH₃SO₃H | 51.4 | Needle-like colorless crystals | 180~185 (decomp.) |
| 22 | 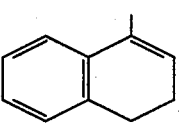 | —CH₂— | —CH(CH₃)₂ | HCl | 53.6 | Needle-like colorless crystals | 224~226 |
| 23 | 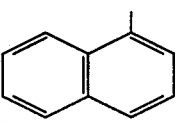 | — | —CH(CH₃)₂ | — | 55.7 | Colorless crystals | 117~119 |

TABLE 2-continued $$R_1-A-COO-\underset{}{\bigcirc}-CON\underset{}{\bigcirc}N-R_2 \quad \text{(Ia)}$$

| Example | R₁ | In Formula (Ia) A | R₂ | Acid Addition Salt | Yield (%) | Appearance | Melting Point (°C.) |
|---|---|---|---|---|---|---|---|
| 24 | 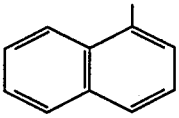 | —CH₂— | —CH(CH₃)₂ | CH₃SO₃H | 81.2 | Colorless crystals | 197~201.5 |
| 25 | 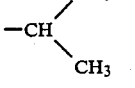 | —OCH₂— | —CH(CH₃)₂ | — | 57.4 | Needle-like colorless crystals | 107~109 |
| 26 | 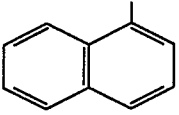 | —CH₂CH₂— | —CH(CH₃)₂ | HCl | 41.0 | Needle-like colorless crystals | 188~191 |
| 27 | 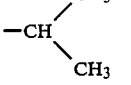 | —CH=CH— | —CH(CH₃)₂ | — | 78.8 | Needle-like colorless crystals | 123~124 |
| 28 | 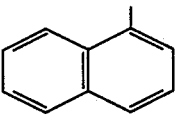 | — | —CH(CH₃)₂ | — | 72.0 | Needle-like colorless crystals | 142~143 |
| 29 | 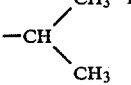 | —CH₂— | —CH(CH₃)₂ | — | 60.1 | Colorless crystals | 115~117 |
| 30 | 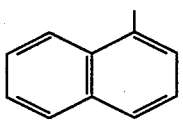 | —OCH₂— | —CH(CH₃)₂ | — | 62.0 | Needle-like colorless crystals | 103~105 |
| 31 | 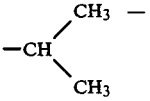 | —CH=CH— | —CH(CH₃)₂ | — | 75.8 | Needle-like colorless crystals | 141~142 |
| 32 | 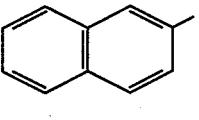 | —CH₂CH₂— | —CH(CH₃)₂ | HCl | 47.4 | Needle-like colorless crystals | 233~234.5 |
| 33 | 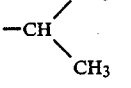 | — | —CH(CH₃)₂ | CH₃SO₃H | 67.2 | Powderous colorless crystals | 200~212 |
| 34 | 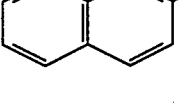 | — | —CH(CH₃)₂ | HCl | 62.2 | Colorless crystals | 213~214 |

TABLE 2-continued $$R_1-A-COO-\underset{}{\bigcirc}-CON\underset{}{\diagup N-R_2}$$ (Ia)

| | In Formula (Ia) | | | Acid Addition Salt | Yield (%) | Appearance | Melting Point (°C.) |
|---|---|---|---|---|---|---|---|
| Example | $R_1$ | A | $R_2$ | | | | |
| 35 | 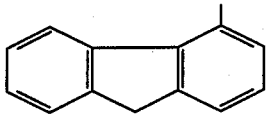 | — | $-CH\diagdown^{CH_3}_{CH_3}$ | — | 46.4 | Needle-like colorless crystals | 95~96 |
| 36 | 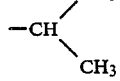 | — | $-CH\diagdown^{CH_3}_{CH_3}$ | — | 44.5 | Prismatic pale yellow crystals | 126~128 |
| 37 | 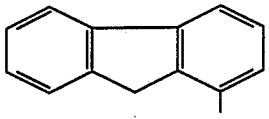 | — | $-CH\diagdown^{CH_3}_{CH_3}$ | — | 40.1 | Needle-like pale yellow crystals | 148~150 |
| 38 | 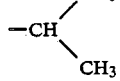 | —CH=CH— | $-CH\diagdown^{CH_3}_{CH_3}$ | — | 54.4 | Pale yellow crystals | 192~195 |
| 39 | 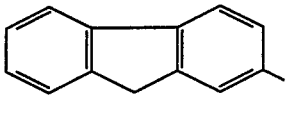 | — | $-CH\diagdown^{CH_3}_{CH_3}$ | HCl | 36.5 | Colorless crystals | 195.5~201 |
| 40 | 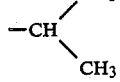 | —CH₂— | $-CH\diagdown^{CH_3}_{CH_3}$ | HCl | 58.0 | Colorless crystals | 225~228 |
| 41 | 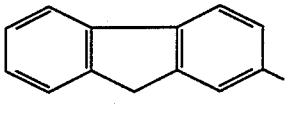 | — | $-CH\diagdown^{CH_3}_{CH_3}$ | — | 63.3 | Prismatic yellow crystals | 134~136 |
| 42 | 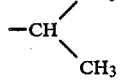 | — | $-CH\diagdown^{CH_3}_{CH_3}$ | — | 66.7 | Platy yellow crystals | 140~147 |
| 43 | 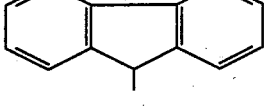 | — | $-CH\diagdown^{CH_3}_{CH_3}$ | — | 14.4 | Prismatic colorless crystals | 181~183 |
| 44 | 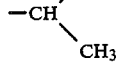 | — | $-CH\diagdown^{CH_3}_{CH_3}$ | (COOH)₂ | 9.6 | Needle-like colorless crystals | 136~139 (decomp.) |

TABLE 2-continued $$R_1-A-COO-\text{C}_6\text{H}_4-CON(\text{piperazine})N-R_2 \quad (Ia)$$

| Example | R₁ (In Formula (Ia)) | A | R₂ | Acid Addition Salt | Yield (%) | Appearance | Melting Point (°C.) |
|---|---|---|---|---|---|---|---|
| 45 | benzofuran-3-yl | — | —CH(CH₃)₂ | — | 45.8 | Colorless crystals | 118~120 |
| 46 | benzofuran-3-yl | —CH₂— | —CH(CH₃)₂ | — | 27.0 | Platy colorless crystals | 117~118 |
| 47 | benzofuran-3-yl | —CH=CH— | —CH(CH₃)₂ | — | 67.6 | Colorless crystals | 159~160 |
| 48 | 7-methoxybenzofuran-3-yl | — | —CH(CH₃)₂ | — | 54.4 | Pale yellow crystals | 92~94 |
| 49 | benzothiophen-3-yl | —CH₂— | —CH(CH₃)₂ | CH₃SO₃H | 75.8 | Pale yellow crystals | 205~207 |
| 50 | chroman-3-yl | — | —CH(CH₃)₂ | CH₃SO₃H | 20.0 | Needle-like colorless crystals | 150~156 |
| 51 | 2H-chromen-3-yl | — | —CH(CH₃)₂ | — | 8.1 | Needle-like colorless crystals | 110~120 |
| 52 | coumarin-3-yl | — | —CH(CH₃)₂ | — | 92.1 | Needle-like colorless crystals | 168~170 |
| 53 | quinolin-4-yl | — | —CH(CH₃)₂ | — | 58.5 | Prismatic colorless crystals | 120~122 |
| 54 | 2-phenylquinolin-4-yl | — | —CH(CH₃)₂ | — | 50.5 | Prismatic pale yellow crystals | 118~120 |

TABLE 2-continued $$R_1-A-COO-\underset{}{\bigcirc}-CON\underset{}{\bigcirc}N-R_2 \qquad (Ia)$$

| Example | In Formula (Ia) R₁ | A | R₂ | Acid Addition Salt | Yield (%) | Appearance | Melting Point (°C.) |
|---|---|---|---|---|---|---|---|
| 55 | 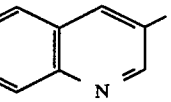 | — | —CH(CH₃)₂ | — | 51.7 | Needle-like colorless crystals | 135~137 |
| 56 | 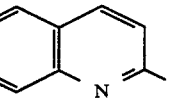 | — | —CH(CH₃)₂ | — | 52.6 | Needle-like colorless crystals | 124~127 |
| 57 | 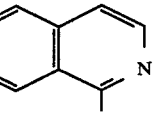 | — | —CH(CH₃)₂ | — | 29.5 | Needle-like pale yellow crystals | 138~140 |
| 58 | 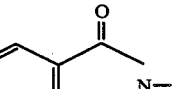 | —CH₂— | —CH(CH₃)₂ | — | 65.4 | Colorless crystals | 113~115 |
| 59 | 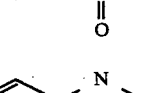 | — | —CH(CH₃)₂ | — | 20.4 | Pale yellow crystals | 103~104 |
| 60 | 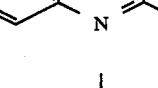 | — | —CH(CH₃)₂ | HCl | 43.1 | Needle-like yellow crystals | 238 (decomp.) |
| 61 | 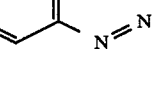 | — | —CH(CH₃)₂ | HCl | 29.6 | Needle-like colorless crystals | 253~255 |
| 62 | 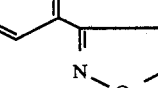 | — | —CH(CH₃)₂ | — | 56.4 | Prismatic colorless crystals | 87~89 |
| 63 | 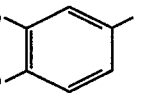 | —CH₂— | —CH(CH₃)₂ | — | 67.4 | Colorless crystals | 113~114.5 |
| 64 | 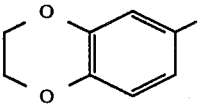 | — | —CH(CH₃)₂ | — | 14.4 | Prismatic colorless crystals | 133~134 |

EXAMPLE 65

1-Methyl-4-[4-(7-methoxyl-1,2,3,4-tetrahydro-1-naphtoyloxy)benzoyl]piperazine.methanesulfonate To a 100 ml solution of actonitrile containing 4.4 g of 1-methyl-4-(4-hydroxybenzoyl)piperazine and 4.94 g of 7-methoxy-1,2,3,4-tetrahydro-1-naphthylcarboxylic acid was added 4.94 g of dicyclohexyl carbodiimide, and the mixture was stirred overnight at room temperature. After removal of any insoluble matter by filtration, the filtrate was concentrated under reduced pressure, incorporated with 50 ml of 0.5N hydrochloric acid and washed with ethyl acetate. After being neutralized with a saturated solution of sodium bicarbonate, the aqueous phase was extracted with ethyl acetate. The extract was washed with water and dried, followed by removal of the solvent by distillation, to obtain a crude oily product. Purification of the product on silica gel column chromatography (eluting solution: chloroform-methanol 30:1) gave 7.57 g of an oily product. The oily product was further converted in a conventional manner to methanesulfonate, thereby obtaining 6.2 g of needle-like pale yellow crystals having a melting point of 150°–151° C. (yield: 61.6%).

EXAMPLES 66–73

The same procedure as in Example 65 was repeated to obtain several compounds shown in Table 3.

TABLE 3

| Example | In Formula (Ia) R₁ | A | R₂ | Acid Addition Salt | Yield (%) | Appearance | Melting Point (°C.) |
|---|---|---|---|---|---|---|---|
| 66 | tetrahydronaphthyl | — | cyclohexyl | CH₃SO₃H | 86.2 | Needle-like colorless crystals | 205~207 |
| 67 | tetrahydronaphthyl | — | —CH(CH₃)₂ | CH₃SO₃H | 89.7 | Needle-like colorless crystals | 180~182 |
| 68 | tetrahydronaphthyl | — | —CH₂CH₃ | CH₃SO₃H | 69.2 | Needle-like colorless crystals | 140~143 |
| 69 | 4-methoxy tetrahydronaphthyl (OCH₃) | — | —CH₃ | — | 56.8 | Colorless oils | — |
| 70 | tetrahydronaphthyl | — | —CH₂—phenyl | CH₃SO₃H | 77.4 | Needle-like colorless crystals | 188~190 |
| 71 | 6-methoxy tetrahydronaphthyl (CH₃O) | — | —CH₃ | — | 42.2 | Oils | — |
| 72 | tetrahydronaphthyl | — | —CH₂(CH₂)₄CH₃ | CH₃SO₃H | 52.5 | Pale yellow crystals | 153~155 |
| 73 | tetrahydronaphthyl | — | —CH₂—cyclohexyl | CH₃SO₃H | 55.4 | Colorless crystals | 227~229 |

EXAMPLE 74

1-Methyl-4-[3-(1,2,3,4-tetrahydro-1-naphthoyloxy)-benzoyl]piperazine.hydrochloride The same procedure as in Example 65 was repeated using 1-methyl-4-(3-hydroxybenzoyl)piperazine and 1,2,3,4-tetrahydro-1-naphthylcarboxylic acid to obtain the title compound having a melting point of 218°-220° C. as needle-like pale yellow crystals (yield: 62.7%).

EXAMPLES 75 AND 76

The same procedure as in Example 74 was repeated to obtain two compounds shown below.

| Appearance | Colorless crystals |
|---|---|
| Melting point | 175-178° C. |
| Yield | 39.5% |
| Appearance | Needle-like pale yellow crystals |
| Melting point | 193-197° C. |
| Yield | 42.6% |

This invention now being fully described, it is apparent to those skilled in the art that many changes and modifications can be made thereto without departing the spirit or scope of the invention set forth herein.

What is claimed is:

1. A benzoylpiperazine ester represented by the formula:

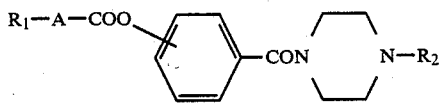

wherein
A represents a single bond or a $C_1$-$C_2$ alkylene group, vinylene group, —O—alkylene group or methine group;
$R_1$ represents a ($C_9$-$C_{11}$) bicyclic carbon ring which may be substituted with a lower alkyl group, lower alkoxy group, oxy group, nitro group or a halogen atom, or may be partially saturated; a fluorene group which may contain an oxo group; a fluorenylidene group; an anthracene group; a phenanthrene group which may be substituted with a lower alkyl group, or may be partially saturated; a benzofuran or thianaphthene group which may be substituted with a lower alkyl group or lower alkoxy group; a benzopyran or benzoazine group which may be substituted with an oxo group or phenyl group or may be partially saturated; a attached through an n atom; a benzodiazine group; an isooxazole which may be substituted with a lower alkyl group or phenyl group; an alkylene dioxybenzene or xanthene group; and
$R_2$ represents an alkyl group, $C_6$ cycloalkyl group, $C_6$ cycloalkyl($C_1$)alkyl group or benzyl group, excepting the case where A is a single bond, $R_1$ is

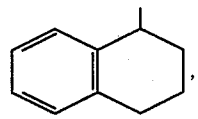

and $R_2$ is a methyl group.

2. A process for producing a benzoylpiperazine ester represented by the formula (I):

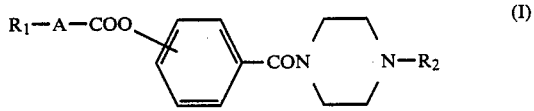

wherein
A represents a single bond or a ($C_1$-$C_2$) alkylene group, vinylene group, —O—alkylene group or methine group;
$R_1$ represents a ($C_9$-$C_{11}$) bicyclic carbon ring which may be substituted with a lower alkyl group, lower alkoxy group, oxo group, nitro group or an halogen atom, or may be partially saturated; a fluorene group which may contain an oxy group; a fluorenylidene group; an anthracene group; a phenanthrene group which may be substituted with a lower akyl group, or may be partially saturated; a benzofuran or thianaphthene group which may be substituted with a lower alkyl group or lower alkoxy group; a benzopyran or benzoazine group which may be substituted with an oxo group or a phenyl group attached through an n atom and may be partially saturated; a phthalimide group; a benzodiazine group; an isooxazole group which may be substituted with a lower alkyl group or phenyl group; or an alkylene dioxybenzene or xanthene group; and
$R_2$ represents an alkyl group, ($C_6$) cycloalkyl group, ($C_6$) cycloalkyl($C_1$)alkyl group or benzoyl group, excepting the case where A is a single bond, $R_1$ is

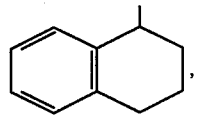

and $R_2$ is a methyl group; which comprises reacting a carboxylic acid represented by the formula (II):

wherein
A and $R_2$ have the same meaning as above or a reactive group thereof, with a substituted phenol represented by the formula (III):

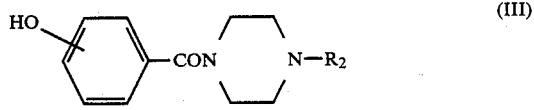

wherein
$R_2$ has the same meaning as above or a reactive group thereof.

3. The benzoylpiperazine ester of claim 1 being 1-isopropyl-4-(4-(5,6,7,8-tetraphydronaphthalene-1-acetyloxy)benzoyl)piperazine hydrochloride.

4. The benzoylpiperazine ester of claim 1 being 1-isopropyl-4-(4-(9-fluorenylidene acetyloxy)benzoyl)piperazine.

5. The benzoylpiperazine ester of claim 1 being 1-isopropyl-4-(4-(thianaphthene-2-acetyloxy)benzoyl)piperazine methanesulfonate.

6. The benzoylpiperazine ester of claim 1 wherein R, is

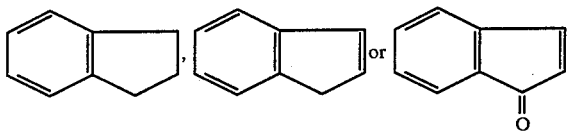

which may be substituted by —CH$_3$ or —OCH$_3$;
R$_2$ is isopropyl; and
A is a single bond, —CH$_2$, or HCl or CH$_3$HSO$_4$ acid addition salts thereof.

7. The benzoylpiperazine ester of claim 1, wherein:
R$_1$ is

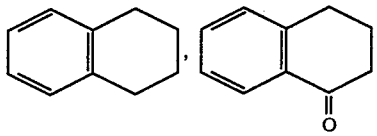

which may have up to 2 more double bonds, or may be substituted by —CH$_3$, —NO$_2$ or Cl;
A is a single bond, —CH$_2$—, —CH$_2$—CH$_2$—, —O—CH$_2$— or —CH=CH—; and
R$_2$ is isopropyl or, HCl or CH$_3$HSO$_3$H acid addition salts thereof.

8. The benzoylpiperazine ester of claim 1 wherein:
R$_1$ is

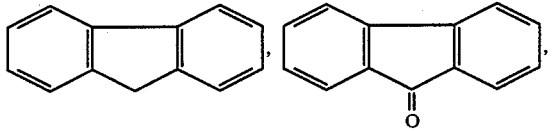

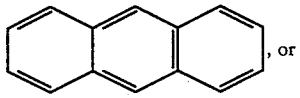

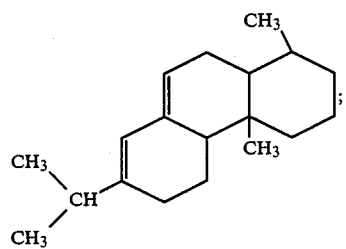

A is a single bond, —CH$_2$— or —CH=CH$_2$; and
R$_2$ is isopropyl or, HCl or (COOH)$_2$ acid addition salts thereof.

9. The benzoylpiperazine ester of claim 1 wherein:
R$_1$ is

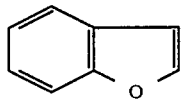

which may be substituted by —OCH$_3$,

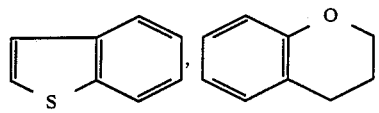

which may have an extra double bond or may be substituted by =O in the C atom next to the —O— atom,

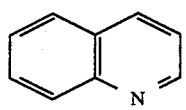

which may be substituted by phenyl,

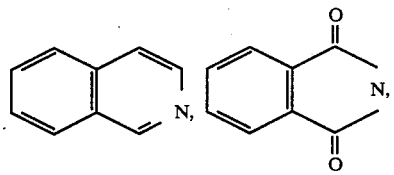

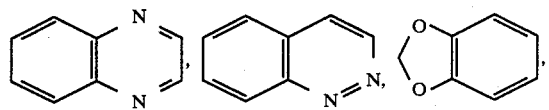

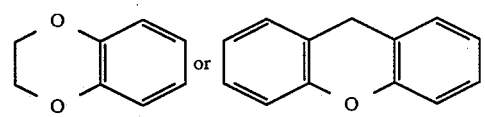

A is a single bond, —CH$_2$ or —CH=CH$_2$—; and
R$_2$ is isopropyl, CH$_3$SO$_3$H or HCl acid addition salts thereof.

10. The benzoylpiperazine of claim 1 being 1-methyl-4-(4-(7-methoxyl-1,2,3,4-tetrahydro-1-naphtoyloxy)-benxoyl)piperazine methanesulfonate.

11. The benzoylpiperazine of claim 1, wherein A is a single bond;
R$_1$ is

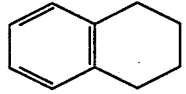

which may be substituted by —OCH$_3$; and
R$_2$ is

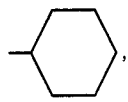

(C$_1$-C$_3$) alkyl, benzyl, —CH$_2$(CH$_2$)$_4$CH$_3$,

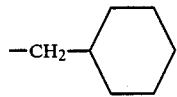

or the CH$_3$SO$_3$H acid addition salt thereof.

12. The benzoylpiperazine of claim 1, being 1-methyl-4-(3-(1,2,3,4-tetrahydro-1-naphthoyloxy)benzoyl)piperazine hydrochloride.

13. The benzoyl piperazine of claim 1, wherein
$R_1$ is a bicyclic carbon ring selected from the group consisting of indanyl, indenyl, indanoyl, naphthyl, dihydronaphthyl, tetrahydronaphthyl, tetrahydronaphthalenoyl and benzocycloheptyl, which may be substituted with lower alkyl, lower alkoxy, nitro, or halogen;
fluorenyl;
fluorenoyl;
fluorenylidinyl;
anthranyl;
phenanthryl which may be substituted with lower alkyl or may be partially saturated;
benzofuryl or thianaphthyl which may be substituted with lower alkyl or lower alkoxyl;
benzopyranyl or benzazinyl which may be substituted with phenyl and may be partially saturated;
benzoazinonyl;
phthalimido;
benzdiazinyl;
isoxazolyl which may be substituted with lower alkyl or phenyl, ($C_1$–$C_2$) alkylene dioxyphenyl or xanthyl; and
$R_2$ is ($C_1$–$C_6$) alkyl, cycloalkyl, cycloalkylmethyl, or benzyl; excepting the case wherein if A is a single bond, $R_1$ is

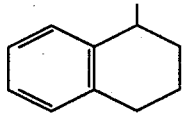

and $R_2$ is methyl.

14. The process of claim 2, wherein
$R_1$ is a bicyclic carbon ring selected from the group consisting of indanyl, indenyl, indanoyl, naphthyl, dihydronaphthyl, tetrahydronaphthyl, tetrahydronaphthalenoyl and benzocycloheptyl, which may be substituted with lower alkyl, lower alkoxy, nitro, or halogen;
fluorenyl;
fluorenoyl;
fluorenylidinyl;
anthranyl;
phenanthryl which may be substituted with lower alkyl or may be partially saturated;
benzofuryl or thianaphthyl group which may be substituted with lower alkyl or lower alkoxyl;
benzopyranyl or benzazinyl which may be substituted with phenyl and may be partially saturated;
benzoazinoyl;
phthalimido;
benzdiazinyl;
isoxazolyl which may be substituted with lower alkyl or phenyl, ($C_1$–$C_2$) alkylene dioxyphenyl or xanthyl; and
$R_2$ is ($C_1$–$C_6$) alkyl, cycloalkyl, cycloalkylmethyl, or benzyl; excepting the case wherein if A is a single bond, $R_1$ is

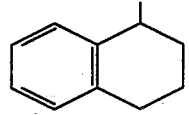

and $R_2$ is methyl.

* * * * *